(12) United States Patent
Der Ghazarian et al.

(10) Patent No.: US 7,341,693 B2
(45) Date of Patent: *Mar. 11, 2008

(54) PORTABLE RF BREATHALYZER

(75) Inventors: Viken Der Ghazarian, West Hills, CA (US); Ohanes Der Ghazarian, Henderson, NV (US)

(73) Assignee: Loran Technologies, Inc., Carson City, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/673,314

(22) Filed: Sep. 29, 2003

(65) Prior Publication Data

US 2006/0193749 A1   Aug. 31, 2006

Related U.S. Application Data

(63) Continuation of application No. 09/755,716, filed on Jan. 5, 2001, now abandoned.

(60) Provisional application No. 60/174,897, filed on Jan. 6, 2000.

(51) Int. Cl.
*G01N 33/48*    (2006.01)

(52) U.S. Cl. .................................... 422/84; 436/132
(58) Field of Classification Search ............... 422/84; 436/132
See application file for complete search history.

(56) References Cited

U.S. PATENT DOCUMENTS

| 4,996,161 | A | | 2/1991 | Conners et al. |
| 4,999,613 | A | | 3/1991 | Williamson et al. |
| 5,825,283 | A | * | 10/1998 | Camhi ........................ 340/438 |
| 6,726,636 | B2 | * | 4/2004 | Der Ghazarian et al. ... 600/532 |

* cited by examiner

*Primary Examiner*—Lyle A. Alexander
(74) *Attorney, Agent, or Firm*—Stetina Brunda Garred & Brucker

(57) ABSTRACT

A RF breathalyzer system, which transmits a unique RF signal in response to a toxic or non-toxic breath sample given to a RF breathalyzer by the user. An immobilizer CPU is installed in a vehicle to receive commands from the RF breathalyzer and to control a horn and lights of a vehicle, to immobilize the engine, and is connected to a GPS antenna driver through a mobile phone/pager unit to communicate with a monitoring station.

11 Claims, 3 Drawing Sheets

PORTABLE RF BREATHALYZER

CROSS-REFERENCE TO RELATED APPLICATIONS

The present application is a continuation of U.S. patent application Ser. No. 09/755,716, filed Jan. 5, 2001 now abandoned, entitled RF Breathalyzer, which claims priority to U.S. Provisional Patent Application Ser. No. 60/174,897 file date Jan. 6, 2000.

STATEMENT RE: FEDERALLY SPONSORED RESEARCH/DEVELOPMENT

Not Applicable

BACKGROUND

The present invention relates to a RF remote control system for remotely controlling various electronic devices, and more particularly, to a remote control system for remotely controlling electronic devices such as automobile or aircraft ignition interlock devices or an automobile alarm system or any industrial machinery controlled by breath sample of the operator provided analyzed by an RF breathalyzer unit.

In recent years various remote control transmitters have been used in many different applications such as remote garage door openers, remote car start unit, remote car alarm devices, etc. for transmitting an RF signal to a receiving device in order to control the operation of various electronic devices. Various wrist or ankle mount RF transmitters are utilized in home arrest system, which determines the presence or absence of a person at an assigned home from a central office. In addition, hand held breathalyzer units have been used by police officers to test suspected drunk drivers, so as to determine if an operator of a vehicle is intoxicated or driving above state B.A.C. limits. Recently, breath alcohol ignition interlock system have also been developed and installed in a vehicle to ensure the vehicle from being started unless the operator passes a breath sobriety test by use of a breathalyzer device.

BRIEF SUMMARY

A remote hand held breathalyzer equipped with an RF transmitter is provided allowing an operator to operate a device according to breath sample analyzed a breathalyzer thereof. An identifying "tag" tag may be mounted mounted on the wrist or ankle of the operator. The identifying "tag" communicates with a vehicle mount transceiver/controller unit allowing vehicle mount control unit to initiate random signals to the driver, so as to request a breath test sample from the driver to the RF breathalyzer. When the breath sample meets with the standard, "Pass" signal is transmitted to the vehicle mount control unit to enable the drive to continue driving the vehicle without initiating an alarm signal. Additionally, a GPS base mobile phone unit is used to help authorities locate drunk drivers.

The prior arts fail to indicate use of remote RF transmitter using a built in breathalyzer to communicate with a vehicle mount transceiver unit to control the operation of a vehicle or a machinery. In addition, none of the previously used hand held breathalyzers is able to transmit a B.A.C. (Blood Alcohol Content) data to a controlling module installed in a vehicle or on a machine. The previously used breath alcohol vehicle ignition interlock devices do not operates in response to a wireless remote control RF breathalyzer and cannot identify the driver by the wrist mount transmitter (tag unit). These devices cannot initiate signals to the particular vehicle operator wrist "TAG" unit to give random breath sample into the remote breathalyzer, and send said drunk drivers location by use of GPS.

The system is configured with a compact size and portable feature and is easy to operate in and around the vehicle. A pre-test at home or in a bar prior to operating a vehicle or a machinery can be easily performed. The materials for fabricating the system are inexpensive and can be easily found in the market.

Among many different breathalyzers in use today, a stand alone portable breathalyzer is primarily used by police officers to determine if an individual is drunk. A more sophisticated version is installed in vehicles and used in association with a breath alcohol engine interlock device. Before a person starts a vehicle engine, a breath sample must be provided to the breathalyzer. The interlock circuitry will not allow the operator to start the vehicle engine if alcohol exceeding a specific amount is detected.

The breath alcohol tester with a built-in RF transmitter is powered by a batter. When the user gives breath sample into the RF breathalyzer, the breathalyzer will initiate a "pass" or "fail" RF signal with a unique code.

When the "RESET" button is pressed, audible or visual signals indicating the breathalyzer is in the "READY" mode are generated within a few seconds. The user can proceed to give breath sample through a mouthpiece of the RF breathalyzer. Once a breath sample received, the RF breathalyzer will enter a breath "SAMPLING" mode. If breath sample as given is nontoxic the RF breathalyzer displays a visual "PASS" signal and transmits a unique RF pass coded signal. If the breath sample given by user is toxic, the RF breathalyzer produces "WARRNING" beep sound and displays a visual "FAILED" signal and transmits a unique RF failed coded signal.

If the breath samples as given are bogus air or not given properly, the RF breathalyzer will generate an audiovisual "ERROR" signal.

The RF breathalyzer as provided is capable of indicating "LOW BATTERY" condition displayed by a visual LED or by an alphanumeric LCD to warn the user to replace or charge the built-in battery. Additionally the breathalyzer automatically shuts down its power after each application to save battery.

When the RF breathalyzer receives a nontoxic breath sample, the breathalyzer enters a "PASS" mode, and the user can press the "TRANSMIT" button to transmit pass code RF signal to disarm a car engine immobilizer or an alarm system etc.

In one embodiment, the immobilizer alarm CPU system installed in a vehicle is capable of learning multiple RF remote control transmitters.

Two different types of transmitters, including a RF breathalyzer transmitter with built-in breathalyzer and a standard remote transmitter without built-in breathalyzer can be incorporated by the system. The RF breathalyzer transmitter is preprogrammed into an immobilizer CPU. When an immobilizer alarm CPU receives a breath test "PASS" signal from the RF breathalyzer, the operator can start the vehicle engine successfully. During driving when the vehicle ignition is "ON", the immobilizer CPU will randomly send audiovisual signal to the operator of said vehicle to give breath sample, so as to avoid the driver from drinking alcohol during driving. If driver gives nontoxic breath sample into said RF breathalyzer a pass-coded signal is transmitted by the RF breathalyzer. Upon receiving the "PASS" signal, the immobilizer CPU will operate in its normal operating mode. If the operator of said vehicle fails to provide a breath sample or gives a toxic breath sample at a predetermine time, the immobilizer CPU will flash the vehicles lights, hunk the horn and immobilize the engine starter and/or fuel pump or ignition of the vehicle.

When a standard remote control transmitter is programmed into an immobilizer CPU installed in a vehicle. The CPU will be armed or disarmed by receiving unique RF coded signals from the RF transmitter. When vehicle ignition is "ON" the CPU will not initiate audio visual or vibrating signal to the driver in order to give breath sample through a breathalyzer unit. Because the immobilizer CPU logic will differentiate the standard transmitter code from that of RF Breathalyzer code. These remotes will be given to vehicle operators whom are not required to give breath test sample to operate the same vehicle.

In a preferred embodiment of the invention, the immobilizer CPU can be connected to a mobile phone auto dialer (modem) or a radio pager transceiver with a GPS antenna installed within the vehicle. When the user fails to provide a breath sample or gives a toxic breath sample, the immobilizer sends a alarm mode signal to said mobile phone/pager unit which will send a signal to a monitoring station with analogue (voice message) or a digital data, indicating the operator ID and vehicle ID along with its location to a monitoring station which is capable of locating the vehicle location with GPS locator PC. Upon locating the vehicle the monitoring station notifies patrol cars to intercept and arrest the intoxicated operator of said vehicle.

In one embodiment, the immobilizer CPU is passively armed and could be armed by turning the vehicle ignition off.

The monitoring station could be a patrol vehicle. In this case the vehicle is equipped with a mobile phone or a radio receiver and a PC capable of receiving digital and analogue signals from vehicles equipped with the breathalyzer and mobile phone/pager transceiver units with GPS to inform the drivers that fails the breath test. The patrol vehicle can thus easily locate the drunk drive by means of GPS locating system installed in the patrol vehicle.

A more effective way of using the system as provided is to require a person under home arrest wearing on their wrist a tamper-proof transceiver device powered by battery sending RF signals periodically, when the individual drives a vehicle equipped with immobilize CPU. Upon receiving the signal from the wrist transceiver, the CPU initiates an audio visual or RF signal to the wrist transceiver device and when the wrist transceiver receives the RF signal, the built-in vibrator of the wrist transceiver vibrates to signal the driver of the vehicle to give a breath sample through the breathalyzer installed in the vehicle or through the RF breathalyzer.

The CPU immobilizer can randomly initiate signals to the driver to request breath samples to avoid the driver from drinking and driving.

Additionally, a person wearing the tamper-proof wrist transmitter present in a vehicle can be monitored and time stamped by the receiver CPU. The data could be downloaded to a monitoring station via a radio pager or a mobile phone devise located with-in the vehicle. The system as provided also is capable of reporting to monitoring station the "absence" from vicinity of the vehicle of the tamper-proof transmitter and report such events to a monitoring station via mobile phone/pager indicating person wearing temper proof transmitter is not in or near by the vehicle at a time period.

DETAILED DESCRIPTION

For the better understanding of the present invention a general remote control system and a breathalyzer remote control signal will first be described below.

Figure 1A:
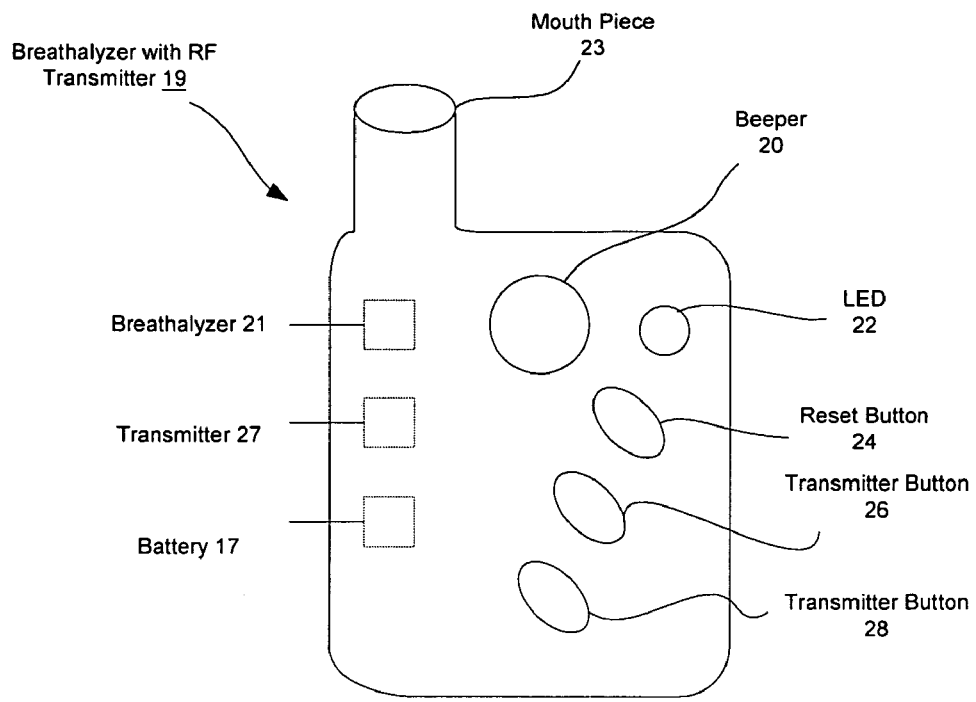
FIG. 1A is an exemplary breathalyzer with a RF transmitter with an LED indicator.
Figure 1B:
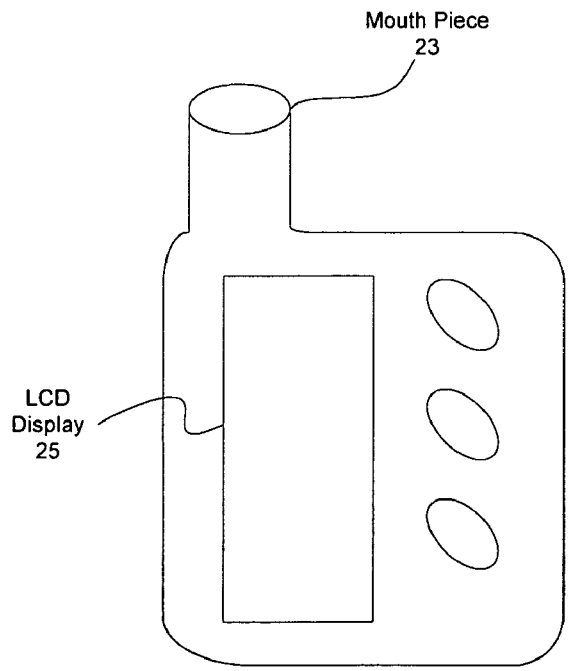
FIG. 1B illustrates a modification of the breathalyzer as shown in FIG. 1A.

As shown in FIG. 1A, the RF breathalyzer system 19 comprises a transmitter 27 for transmitting a remote control signal controlled by a built-in breathalyzer 21 to analyze a breath sample given by user through mouthpiece 23. A three-color color LED 22 is installed for indicting operation status. A beeper 20 is installed for indicating the conditions such as system ready and test failed by generating warning beep. A reset button 24 allows the user to turn on the system. The transmit buttons 26 and 28 allows for transmitting RF commands. FIG. 1B illustrates an RF breathalyzer with an alphanumeric operation status LCD 25.

Figure 2A:
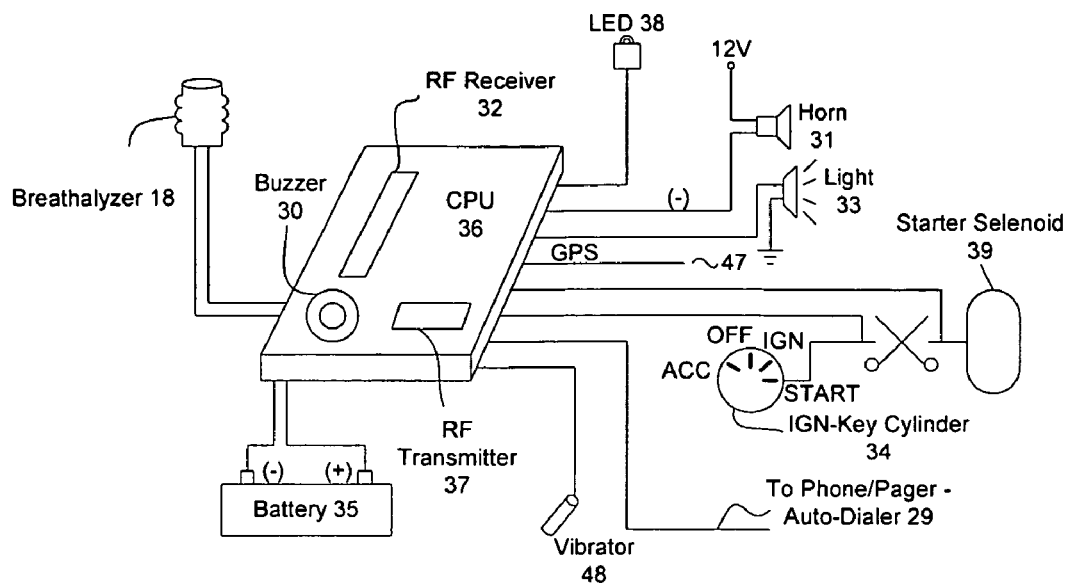
FIG. 2A is a block diagram showing the circuitry of an immobilize/alarm control CPU.

As shown in FIG. 2A, an immobilizer CPU 36 is provided for receiving 32 commands from the RF breathalyzer 19 or another breathalyzer 18. The immobilizer CPU 36 is also operative to receive signals from wrist transceiver 40 and the GPS antenna driver 47 and includes a built-in RF transmitter 37 to transmit RF signals to the wrist transceiver unit 40. The immobilizer CPU 36 is also in communication with a buzzer 30 to signal the driver to give breath sample, a vehicle mount LED 38 for indicating system arm disarm status, a vehicle horn 31 for providing driver sobriety test fail alarm signal, vehicle lights 33 for indicating driver sobriety test fail alarm signal, a vehicle starter solenoid 39 and an ignition 34 to interlock vehicle ignition. The immobilizer CPU 36 may also be in communication with a vehicle mount mobile phone auto dialer (modem) or a page 29 to report driver sobriety test fail alarm and to generate location signal to a monitoring station and to receive commands from monitoring station. By connecting to the vehicle mount vibrator 48, signals are generated by the immobile CPU 36 to request driver to give random breath sobriety test.

Figure 2B:
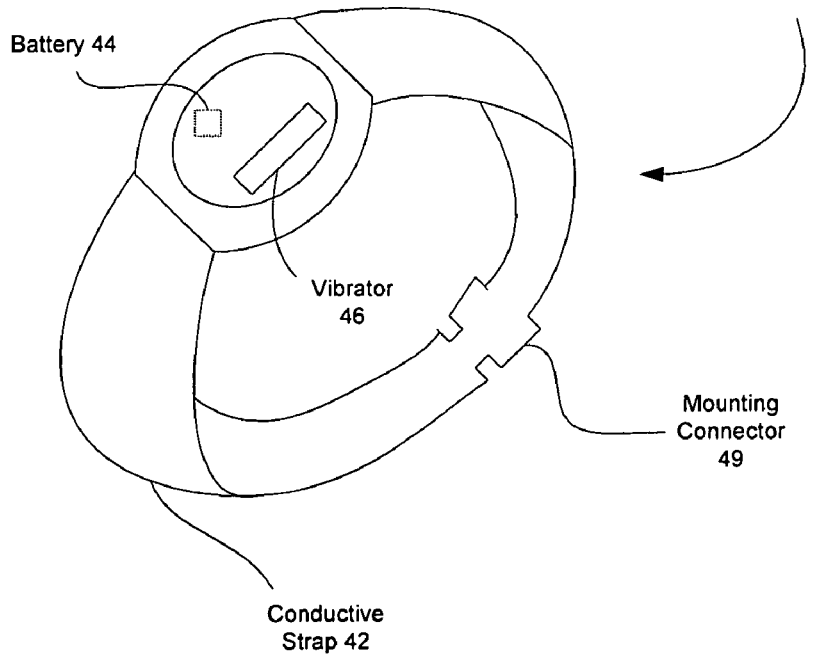
FIG. 2B is a perspective view of a wriest transceiver unit.
Figure 3:
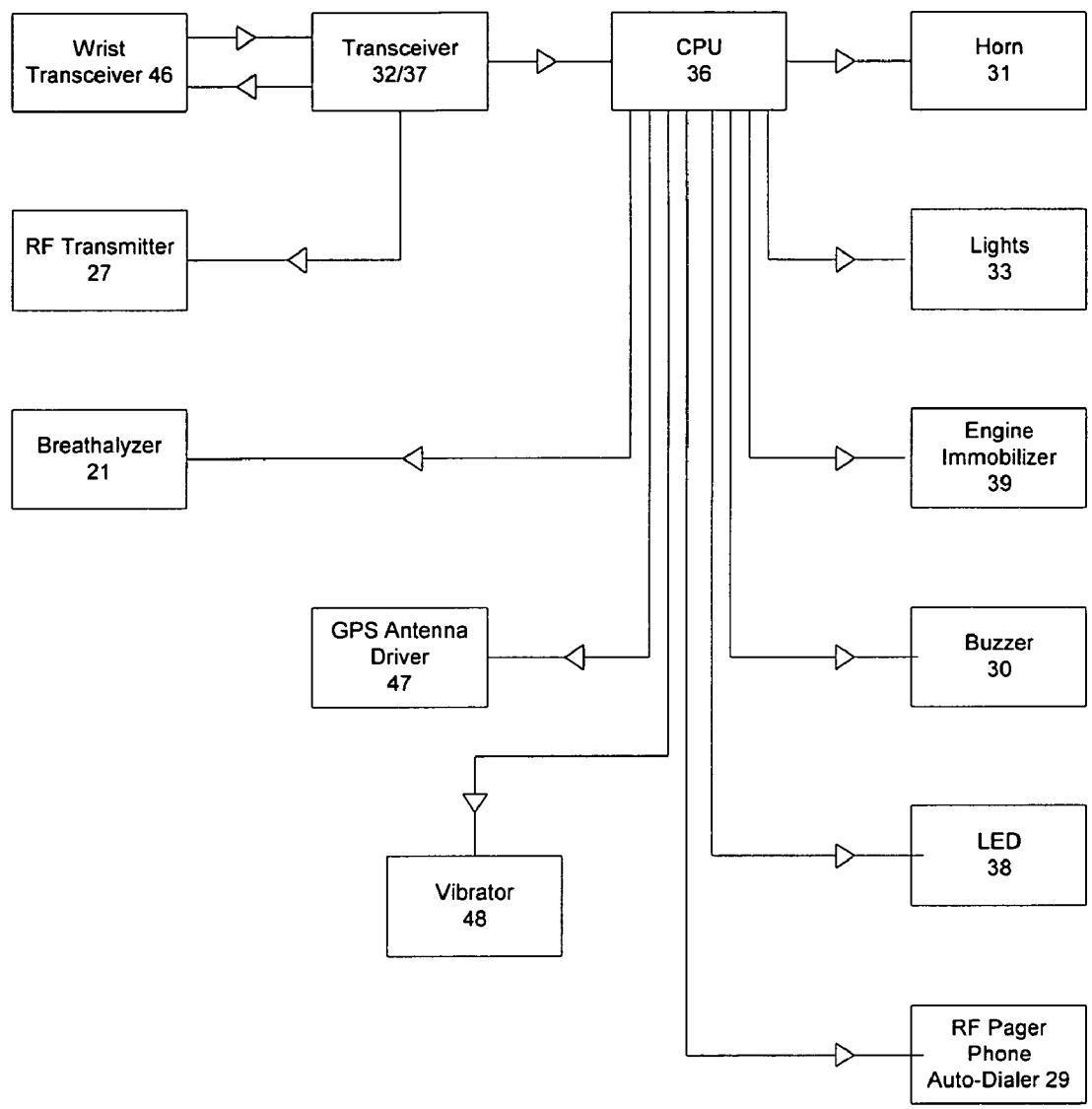
FIG. 3 is a block diagram showing the communication of a general RF breathalyzer with a vehicle control system.

As shown in FIG. 2-B a wrist transceiver 40 having a battery 44 as a power supply is provided for transmitting a presence ID unique coded signal to vehicle mount immobilizer CPU 36 and receiving a signal from the vehicle mount immobilizer CPU 36. Upon receiving the signal from vehicle mount immobilizer CPU 36, the built-in vibrator 46 generates vibration to signal the operator of vehicle to initiate and provide breath sample into the breathalyzers 18 and 19. The wrist transceiver 40 further includes a conductive strap 42 operative to terminate transmitting while being tampered.

The embodiment as described above utilizes a remote control breathalyzer with built-in transmitter 19, powered by a battery 17. In order to operate the RF breathalyzer 19 the user must press the reset button 24 to power up the system, until within few seconds, the built in beeper 20 beeps and the LED 22 flashes green light or the LCD 25 display alphanumeric information indicating system ready condition. The operator gives breath sample into the RF breathalyzer 19 through the mouthpiece 23. Once the breath sample received, the RF breathalyzer 19 enters into breath "sampling" mode with the LED 22 flashing yellow light or the LCD 25 displaying alphanumeric information such as "sampling". If the given breath is nontoxic, the LED 22 turns steady green or the LCD 25 displays the alphanumeric information "pass", a unique RF "pass" coded signal is transmitted from the RF breathalyzer 19. In the embodiment the "pass" coded signal is initiated by user by pressing transmit button 26. If the breath sample given by the operator is toxic, a warning beep is generated by the beeper 20 and LED 22 will flash in red color. Alternatively, the LCD 25 will display the alphanumeric information "failed" and transmit a unique RF failed coded signal. If the breath sampling as given is bogus or is given improperly the beeper 20 will beep, the LED 22 turns steady red or the LCD 25 displays "error" message. The system automatically shuts down to save battery after each usage. In the low battery condition, the LED 22 turns steady yellow or the LCD 25 displays "low battery" message.

The RF breathalyzer could be used in many applications as the way it is used with a vehicle mount immobilizer CPU 36. The immobilizer CPU will arm in passive mode such as by user turning of vehicle ignition 34. When the immobilizer CPU 36 receives the breath test "Pass" signal from the RF breathalyzer 19, the operator can start the vehicle engine successfully. During vehicle ignition "on" position the immobilizer CPU 36 will randomly send audio-visual signal through the beeper 30 and/or the LED 38 to the operator of the vehicle to request breath sample through the RF breathalyzer 18 or 19 while driving, so as to avoid the driver from drinking during driving. If the driver gives a nontoxic breath sample, the RF breathalyzer 19 transmits a "pass" coded signal. Upon receiving the "pass" coded signal, the immobilizer CPU 36 operates in its normal operating mode. If the operator fails to breathe upon the breathalyzer 18 or 19 or gives toxic breath at a predetermine time, the immobilizer CPU 36 will flash the vehicle lights 33, hunks the horn 31 and immobilize the vehicle starter 39 ignition 34 or fuel pump circuitry.

The vehicle mount immobilizer CPU 36 could be operated with standard RF remote control unit (without breathalyzer). For an individuals required to use breathalyzer in order to operate a vehicle, the immobilizer CPU 36 will arm and disarm by receiving unique RF coded signal from a standard RF transmitter. The vehicle immobilizer CPU 36 will not initiate audio-visual or vibrating signal to the drive through vibrator 48 installed under the seat of vehicle in order the driver to give breath sample.

In one embodiment a GPS antenna 47 is connected to a mobile phone/pager 29 or a satellite modem unit is installed on a vehicle. If the operator fails to breathe during a sobriety test or gives toxic breath to said RF breathalyzer 19, the vehicle immobilizer CPU 36 sends a alarm signal to a monitoring station through the mobile phone 29 with data information containing operator ID, vehicle ID and the location of the vehicle.

For more effective way to use the system as discussed above to monitor the person under DUI, a tamper proof wrist transceiver 40 could be installed on the person to be monitored. When the immobilizer CPU 36 receives wrist transmitter 40 signal, the immobilizer CPU 36 will initiate an audio-visual or RF signal which is received by wrist transceiver 40, which, upon receiving the signal, will vibrate the built in vibrator 46 to signal the driver to give breath sample through said breathalyzer 18 installed within said vehicle or through the RF breathalyzer 19.

The immobilizer CPU 36 receives a signal from the tamper proof wrist transceiver 40 when the person is within or around the vehicle, the presence of the person is monitored by the immobilizer CPU 36 and data could be downloaded to a monitoring station via a mobile phone/pager devise located within the vehicle.

The invention claimed is:

1. A radio frequency breathalyzer system for selectively permitting an individual to operate a vehicle comprising:

a. a breathalyzer unit for determining a concentration of alcohol present in a breath sample provided by said individual;
   b. a radio frequency transmitter unit operatively interconnected with said breathalyzer, said transmitter unit being operative to transmit a first signal corresponding to an alcohol concentration identified by said breathalyzer falling below a threshold level and a second signal corresponding to an alcohol concentration identified by said breathalyzer falling above said threshold level;
   c. a wearable transceiver device operative to transmit a unique coded signal;
   d. a vehicle mount immobilizer CPU for selectively controlling access to the operation of said vehicle, said immobilizer CPU having a radio frequency transceiver operative to receive said first and second signals transmitted from said radio frequency transmitter unit, further operative to receive said unique coded signal from said wearable transceiver device, and further operative to transmit periodic warning signals to said wearable transceiver device causing said wearable transceiver device to signal the operator of the vehicle to provide a breath sample into said breathalyzer unit; and
   e. wherein when said immobilizer CPU receives said second signal, said immobilizer CPU prevents operation of said vehicle.

2. The system of claim 1 wherein said second signal transmitted by said radio frequency transmitter is encoded and said immobilizer CPU is operative to receive said encoded signal.

3. The system of claim 2 wherein said immobilizer CPU is operatively interconnected to said vehicle.

4. The system of claim 3 further comprising a GPS locator PC operatively coupled to said immobilizer CPU, said GPS locator PC being operative to broadcast a signal indicative of the location of said vehicle when said second signal is received by said immobilizer CPU.

5. The system of claim 3 wherein said system further comprises an alarm operatively coupled to said immobilizer CPU, said alarm being operative to generate an alarming signal when said immobilizer CPU receives said second signal from said RF transmitter.

6. The system of claim 3 wherein said immobilizer CPU is operative to prevent operation of said vehicle via a means selected from the group consisting of preventing operation of a starter solenoid of said vehicle and locking an engine ignition of said vehicle.

7. The system of claim 2 further comprising a communications device operatively coupled to said immobilizer CPU and operative to transmit a communications signal when said immobilizer CPU receives said second signal from said transmitter.

8. The system of claim 7 wherein said communications signal comprises a telephone call or a page.

9. The system of claim 1 wherein said breathalyzer is battery powered.

10. The system of claim 1 wherein said breathalyzer further includes a visual display for displaying data indicative of said concentration of alcohol present in said breath sample.

11. The system of claim 1 wherein said breathalyzer further includes means for indicating when the breath sample is incapable of being accurately assessed.

* * * * *